United States Patent [19]

Yamaguchi et al.

[11] Patent Number: 5,071,537
[45] Date of Patent: Dec. 10, 1991

[54] REFERENCE ELECTRODE

[75] Inventors: Shuichiro Yamaguchi, Fuji; Norihiko Ushizawa; Takeshi Shimomura, both of Fujinomiya, all of Japan

[73] Assignee: Terumo Kabushiki Kaisha, Tokyo, Japan

[21] Appl. No.: 298,744

[22] PCT Filed: Jul. 9, 1987

[86] PCT No.: PCT/JP87/00491
§ 371 Date: May 8, 1989
§ 102(e) Date: May 8, 1989

[87] PCT Pub. No.: WO88/00700
PCT Pub. Date: Jan. 28, 1988

[30] Foreign Application Priority Data

Jul. 10, 1986 [JP] Japan .................. 61-160932
Jul. 21, 1987 [JP] Japan .................. 61-169938

[51] Int. Cl.⁵ .......................................... G01N 27/31
[52] U.S. Cl. .................................. 204/414; 204/435; 264/61; 427/126.1; 427/126.5
[58] Field of Search .................................. 204/414, 435

[56] References Cited

U.S. PATENT DOCUMENTS

| | | | |
|---|---|---|---|
| 3,806,439 | 4/1974 | Light et al. | 204/435 |
| 3,833,495 | 9/1974 | Grubb | 204/435 |
| 3,856,636 | 12/1974 | Grubb | 204/435 |
| 4,116,798 | 9/1978 | Magar | 204/435 |
| 4,282,081 | 8/1981 | Arrance | 204/435 |
| 4,305,802 | 12/1981 | Koshiishi | 204/418 |
| 4,568,444 | 2/1986 | Nakamura et al. | 204/435 |
| 4,613,422 | 9/1986 | Lauks | 204/419 |
| 4,706,678 | 11/1987 | Otten et al. | 204/435 |
| 4,753,719 | 6/1988 | Yamaguchi et al. | 204/418 |
| 4,798,664 | 1/1989 | Yamaguchi et al. | 204/418 |
| 4,816,118 | 3/1989 | Oyama et al. | 204/418 |
| 4,839,020 | 6/1989 | Yamaguchi et al. | 204/431 |
| 4,861,454 | 8/1989 | Ushizawa et al. | 204/414 |
| 4,913,793 | 4/1990 | Leonard | 204/435 |

FOREIGN PATENT DOCUMENTS

| | | |
|---|---|---|
| 160566 | 11/1985 | European Pat. Off. |
| 50-117490 | 9/1975 | Japan . |
| 53-48595 | 5/1978 | Japan . |

OTHER PUBLICATIONS

Ives et al., "Reference Electrodes, Theory and Practice", 1961, pp. 333-335.

*Primary Examiner*—T. Tung
*Attorney, Agent, or Firm*—Burns, Doane, Swecker & Mathis

[57] ABSTRACT

A miniature, solid-state long-life reference electrode in which the amount of outflow of an internal electrolyte containing a halogen ion is reduced includes a conductor on the periphery of which is formed a sintered body consisting of a silver halide and silver oxide, a water-containing gel enveloping the conductor and including a halogen ion electrolyte, and a hollow tubular body closed by a liquid-junction portion comprising a porous ceramic, or by a partitioning wall having an ion permeable portion of a predetermined diffusion coefficient and volume. In another embodiment, the tubular body of the reference electrode is partitioned by a partitioning wall having an ion permeable portion of a predetermined diffusion coefficient and volume.

21 Claims, 7 Drawing Sheets

REFERENCE ELECTRODE

BACKGROUND OF THE INVENTION

1. Field of the Invention

This invention relates to a reference electrode and, more particularly, to a reference electrode used in measuring ion concentration, gas concentration and the like. Further, the invention relates to a reference electrode capable of operating stably for an extended period of time in a biological system or circulating circuit system.

2. Description of the Prior Art

Examples of reference electrodes (also referred to as comparison electrodes) known in the art include saturated calomel electrodes and silver/silver chloride electrodes. These reference electrodes are readily available on the market and comprise a glass tube accommodating a saturated potassium or sodium chloride solution and an electrode. Formed in the distal end portion of the tube is a liquid-junction portion through which the solution of potassium or sodium chloride is allowed to flow out. When a measurement is to be taken in a living body or body fluid, use of the saturated calomel electrode is hazardous since the electrode relies upon mercury. In such cases, therefore, the silver/silver chloride electrode is employed However, the outflow of the potassium or sodium chloride solution in the latter electrode has a great effect upon a living body. For this reason, the liquid-junction portion is formed of a porous material to reduce the amount of outflow. Nevertheless, fully satisfactory results are not obtained.

Another disadvantage of the conventional reference electrode is that the electrode is used in a living body or in a circuit system through which a body fluid circulates, the potential of the electrode is rendered unstable by changes in temperature. Though a potential which remains stable for a long period of time can be obtained by adding a large quantity of potassium or sodium chloride crystals to the internal liquid chamber of the electrode or adopting a porous body as the liquid-junction portion, these expedients make it difficult to miniaturize the electrode.

Another type of reference electrode is adapted to enable replenishment of the sodium chloride which has flowed out. Such an electrode enjoys a comparatively long service life. However, in order to allow this reference electrode to operate stably for an extended period of time in a biological system or circulating circuit and to be integrated with any of a variety of sensors such as an ion sensor, the electrode is required to be of the solid-state type, small in size and possessed of a long life. However, a solid-state electrode of this kind does not enable the electrolyte to be replenished or replaced, and an expedient must be devised that reduces the amount of electrolyte outflow.

SUMMARY OF THE INVENTION

Accordingly, an object of the present invention is to provide a miniature, solid-state reference electrode which can be used safely in vivo or in a body fluid and stably, for an extended period of time, in vivo or in a circulating circuit, and which will not respond to the pH of a specimen or be influenced by a temperature.

According to the invention, the reference electrode includes a liquid-junction portion formed of a porous ceramic, an electrode portion composed of an electrical conductor, which comprises platinum or silver, and a sintered body formed on the periphery of the conductor and containing silver halide and silver oxide. The electrode portion is enveloped by a water-containing gel containing a halogen ion electrolyte.

More specifically, the reference electrode of the present invention comprises: an electrode portion having an electrical conductor consisting of platinum or silver, and a sintered body formed on the periphery of the conductor and consisting of silver halide and silver oxide; a water-containing gel enveloping the electrode portion and containing halogen ion; a hollow tubular body accommodating the water-containing gel and having one end closed by a liquid-junction portion comprising a porous ceramic and its other end liquid-tightly sealed by a plug; and a conductor wire connected to the conductor and extended to pass through the plug liquid tightly.

The porous ceramic has voids through which at least halogen ions are capable of passing.

Since the liquid-junction portion is formed of a porous ceramic, outflow from the source of halogen ion supply is suppressed, thereby enhancing the safety of the reference electrode. Furthermore, since the electrode portion includes the sintered body comprising silver halide and silver oxide formed on the periphery of the platinum or silver conductor and, moreover, since the water-containing gel contains halogen ion, the potential of the electrode exhibits little dependence upon temperature. In addition, the reference electrode of the invention has a simple structure, is readily manufactured and can be reduced in size. The reference electrode is well-suited for measuring the concentration of body fluid constituents where sterilization by heat is required.

In another aspect of the invention, a reference electrode comprises: an electrode portion comprising an electrical conductor consisting of platinum or silver, and a silver halide and silver oxide formed on the periphery of the conductor; a water-containing gel enveloping the electrode portion and containing a halogen ion electrolyte; an ion impermeable partitioning wall partitioning the water-containing gel into at least two portions; an ion permeable portion, which is permeable to the ions constituting the electrolyte, running through the partitioning wall and having a predetermined diffusion coefficient and volume; a hollow insulative tube accommodating the water-containing gel and having one end closed by a liquid-junction portion comprising a first plug and its other end liquid-tightly sealed by a second plug; and a conductor wire connected to the conductor and extended to the exterior of the hollow insulative tube by being passed through the second plug liquid tightly.

In still another aspect of the invention, a reference electrode comprises: an electrode portion comprising an electrical conductor consisting of platinum or silver, and a silver halide and silver oxide formed on the periphery of the conductor; a water-containing gel enveloping the electrode portion and containing a halogen ion electrolyte; an ion impermeable partitioning wall partitioning the water-containing gel into at least two portions; a first ion permeable portion, which is permeable to the ions constituting the electrolyte, running through the partitioning wall and having a predetermined diffusion coefficient and volume; a hollow insulative tube accommodating the water-containing gel and having one end closed by a liquid-junction portion comprising a first plug and its other end liquid-tightly sealed by a second plug; a second ion permeable portion, which is permeable to the ions constituting the electrolyte, running through the liquid-junction portion and having a predetermined diffusion coefficient and volume; and a conductor wire connected to the conductor and extended to the exterior of the hollow insulative tube by being passed through the second plug liquid tightly.

Preferred embodiments of the invention are as follows:
1. The diffusion coefficient of the ion permeable portion ranges from $10^{-7}$ to $10^{-10}$ cm$^2$/sec and the volume thereof ranges from 0.01 to 6 mm$^3$.
2. The ion permeable portion comprises an ion exchange resin layer.
3. The ion permeable portion comprises an anion exchange resin layer and a cation-exchange resin layer.
4. The ion permeable portion comprises a hollow fiber filled with the water-containing gel containing the halogen ion electrolyte.
5. The hollow fiber comprises an ion permeable hydrophilic polymer or an ion permeable hydrophobic polymer.

Thus, in accordance with the invention, there is provided a miniature, solid-state reference electrode which can be used safely in vivo or in a body fluid and stably, for an extended period of time, in vivo or in a circulating circuit, and which will not respond to the pH of a specimen or be influenced by a fluctuation in temperature.

Other advantages of the reference electrode according to the invention are as follows:
1. Potential is stable without being influenced by the pH of a solution or by the $CO_2$ and $O_2$ concentration of the solution.
2. Since there is no temperature coefficient, there is no influence from fluctuations in temperature.
3. The electrode has a long life despite its small size. The electrode is particularly suitable for extended use in a circulating circuit.
4. The electrode is simple in structure and readily manufactured.
5. Since the electrode has a solid-state structure, it can be used in any attitude whatsoever.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Preferred embodiments of the present invention will now be described with reference to the drawings.

Figure 1:
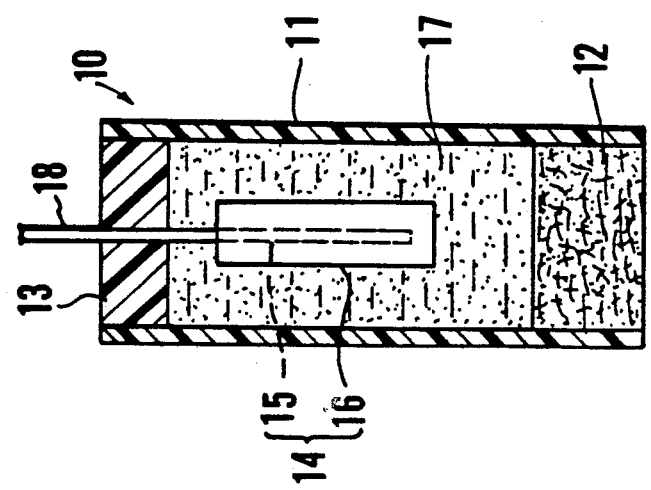
FIG. 1 is a sectional view illustrating a reference electrode according to Examples 1 through 6 of the present invention.

As shown in FIG. 1, a reference electrode 10 in accordance with the invention has an insulative hollow tubular body 11 such as a Teflon tube or the like. One end of the tubular body 11 is closed by means of a liquid-junction portion 12 consisting of a porous ceramic. Any porous ceramic permeable to ions applied for generation of a potential at an electrode section, described below, can be used. Examples of these ions are hydrogen ion and halogen ion. Especially preferred as the porous ceramic is a sintered mixture of zirconium silicate ($ZrSiO_4$) and carbon. Specifically, a sintered body can be formed by preparing a mixture of zirconium silicate powder and carbon powder at a weight ratio of from 100:1 to 100:50, compacting the mixture into a predetermined shape, e.g. a disk-shaped configuration, and sintering the mixture at a temperature of from 800° C. to 1,300° C. This liquid-junction portion comprising the sintered body of zirconium silicate and carbon will not be influenced by the pH of a liquid specimen. In addition, a silver chloride complex eluted by halogen ion will not deposit on this liquid-junction portion and clog the same. This assures that a stable potential will be obtained.

The hollow tubular body 11 accommodates an electrode section 14 comprising a wire-like conductor 15 consisting of platinum or silver, and a sintered body 16 formed about the conductor 15. The sintered body 16 contains a silver halide, particularly silver chloride, and silver oxide. The sintered body 16 can be formed by preparing a mixture of silver halide powder and silver oxide powder at a weight ratio of from 95:5 to 5:95, compacting the mixture onto the periphery of the conductor 14 to coat the same, and then sintering the mixture at a temperature of from 300° C. to 500° C.

The interior of the hollow tubular body 11 is filled with a water-containing gel 17 enveloping the electrode section 14. Examples of the water-containing gel 17 that can be used include polyvinyl alcohol, polyacryl amide, agar-agar, gelatin, a natural high polymer, mannan or starch.

The water-containing gel 17 contains a halogen ion, of which sodium chloride is the most suitable source of supply since any outflow into a liquid biological specimen will have almost no harmful effects. Ordinarily, the sodium chloride is contained in the gel 17 at a ratio of from 0.1 mol/l to 4.52 mol/l. Preferably, a trace amount (e.g. 0.0002 wt % to 0.001 wt %) of silver chloride is added to the water-containing gel 17.

The end of the hollow tubular body 11 opposite the liquid-junction portion 12 is liquid-tightly sealed by an insulative plug 13 penetrated liquid tightly by a conductor wire 18, whereby the electrode section 14 is led out to the exterior of the tubular body 11. The insulative plug 13 preferably comprises a silicon bonding agent, an epoxy resin or the like. Preferably, the conductor wire 18 constitutes a portion of the conductor 15.

EXAMPLES 1 AND 2, AND COMPARISON EXAMPLES 1 AND 2

Two examples of the reference electrode 10 having the construction shown in FIG. 1 were prepared as follows:

A mixture consisting of 100 parts by weight of zirconium silicate powder and 30 parts by weight of carbon powder was compressed to be molded into a disk having a diameter of 1 mm, and the disk was sintered in an electric furnace at a temperature of 1,200° C. for 1 hr to fabricate the liquid-junction portion 12. A mixture consisting of 60 parts by weight of silver chloride powder and 40 parts by weight of silver oxide powder was compressed into a cylindrical body to coat the distal end portion of a platinum wire having a diameter of 0.2 mm. This was then sintered in an electric furnace at a temperature of 400° C. for 15 min to fabricate the electrode section 14 having the conductor wire 18.

The liquid-junction portion thus fabricated was inserted into the distal end portion of the tubular body 11, consisting of a heat-shrinkable Teflon tube having a diameter of about 1 mm, the electrode section 14 was inserted into the tube 11, and the tube 11 was filled with the gel 17, consisting of agar-agar, containing sodium chloride in the proportions shown in the Table hereinbelow. The plug 13, consisting of epoxy resin, was inserted into the other end of the tube 11, thereby completing the fabrication of the reference electrode 10.

TABLE 1

| Reference Electrode | NaCl Concentration (mol/l) |
|---|---|
| Example 1 | 3 |
| Example 2 | Saturated (approximate 4.52 mol/l) |
| Comparison Example 1 | 0.154 |
| Comparison Example 2 | 1 |

EXPERIMENT 1

Figure 2:
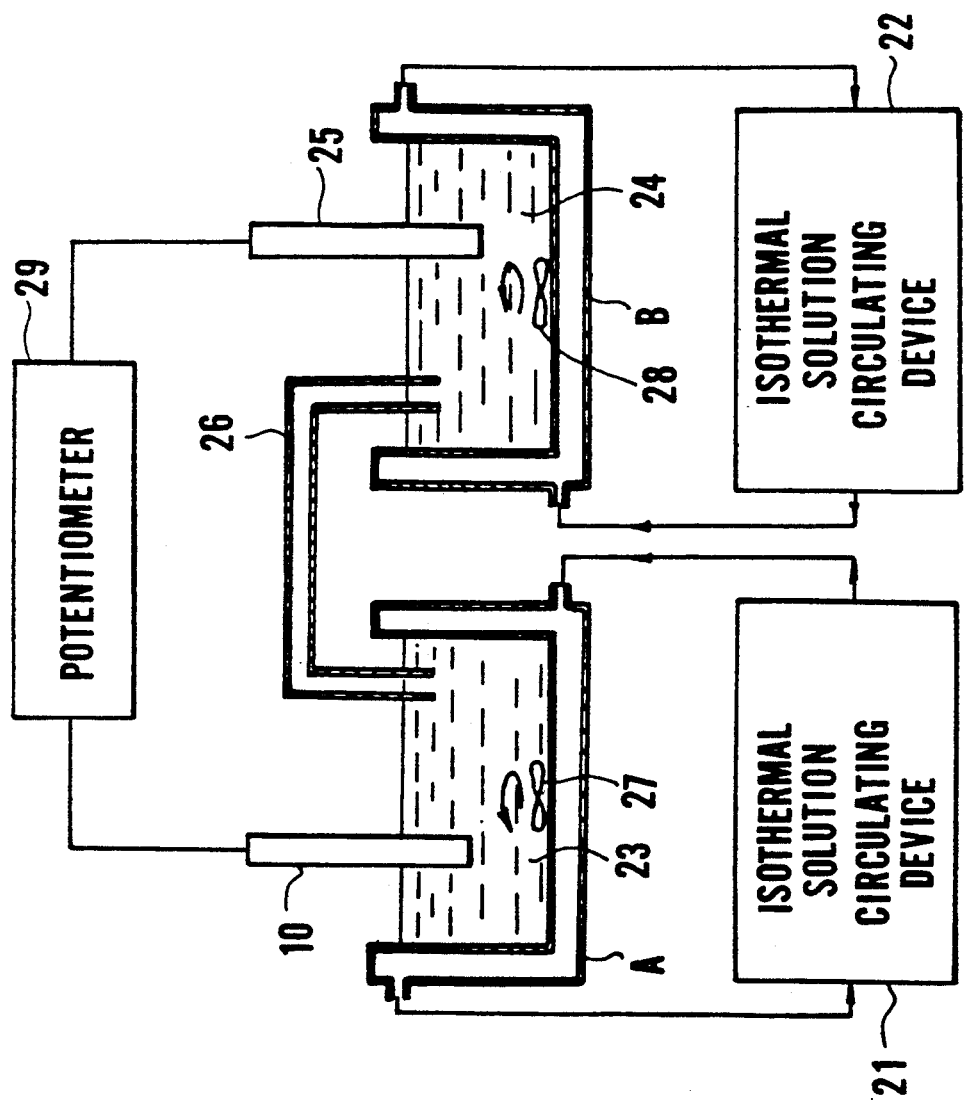
FIG. 2 is a schematic view of a measuring apparatus for measuring the characteristics of the reference electrode according to Examples 1, 2, 5 and 6 of the present invention.

The apparatus shown in FIG. 2 was used to examine the temperature dependence of the potential exhibited by the reference electrodes fabricated in accordance with Examples 1 and 2.

The apparatus of FIG. 2 included identically constructed cells A and B each having an isothermal jacket within which an isothermal solution was circulated by respective isothermal solution circulating devices 21 and 22. The cells A and B were respectively filled with 50 mM phosphate buffer solutions 23 and 24 each containing 0.154 M sodium chloride at pH 7.4. Each reference electrode 10 of the present invention was immersed in the buffer solution 23 of cell A, and a readily available saturated sodium chloride calomel electrode (hereinafter referred to as an "SSCE") 25 was immersed in the buffer solution 24 of cell B. A liquid junction was formed between the two cells by a saturated sodium chloride agar-agar salt bridge 26, and magnetic stirrers 27, 28 were provided with the cells A, B. The potential difference between the reference electrode 10 and SSCE 25 was measured by a potentiometer 29.

Figure 3:
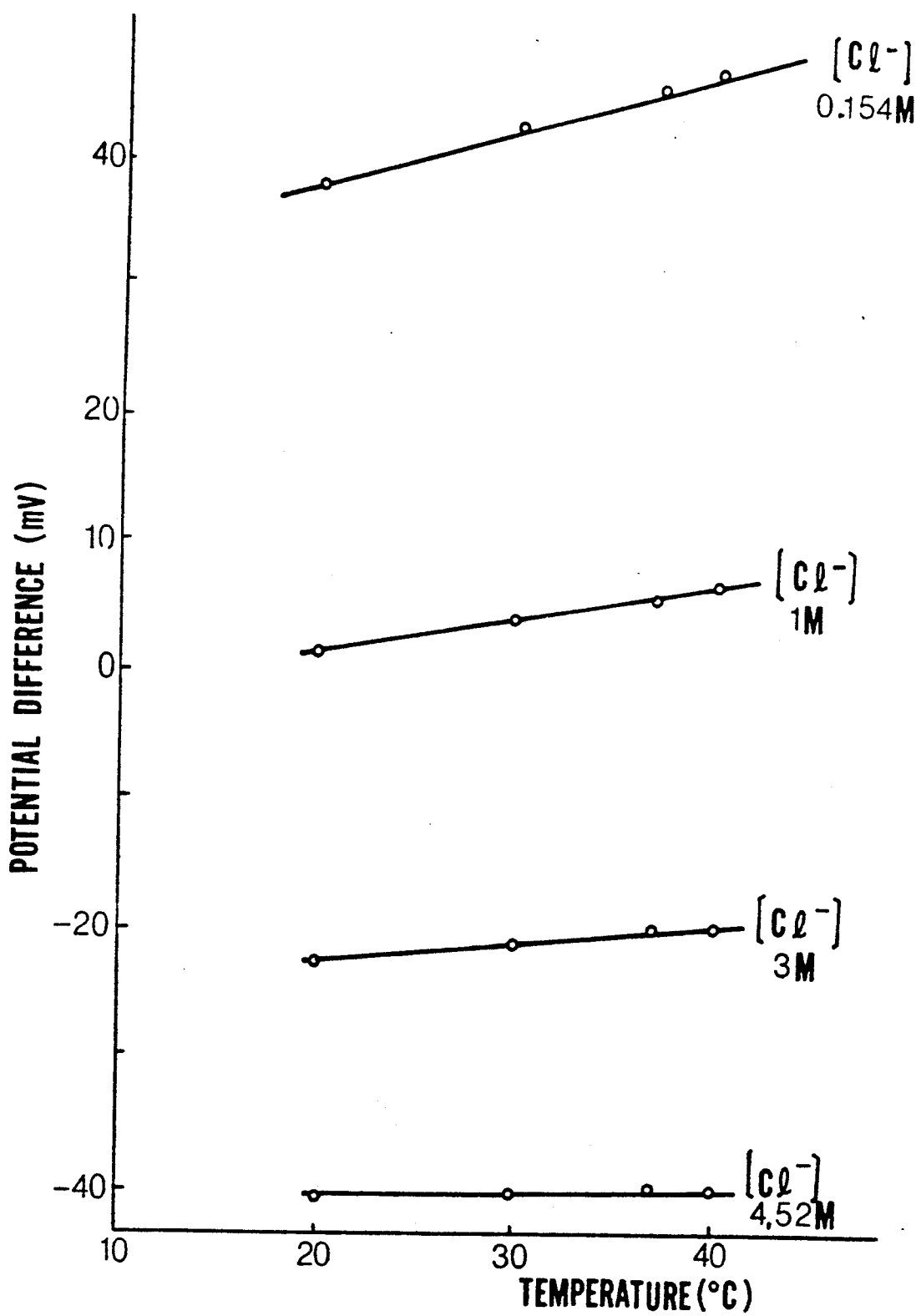
FIG. 3 is a graph illustrating characteristics of the reference electrode according to Examples 1 and 2 of the present invention.

The solution temperature in cell B was held constant at 25° C. by the isothermal circulating device 21, and the solution temperature in cell A was held constant at 20° C., 30° C., 37° C. and 40° C. The potential difference at each of these latter four temperatures was measured by potentiometer 29. The results are as shown in Table 2 and FIG. 3.

TABLE 2

| | Potential Difference (mV) | | | |
|---|---|---|---|---|
| Reference Electrode | 20° C. | 30° C. | 37° C. | 40° C. |
| Example 1 | −22.47 | −21.28 | −20.32 | −20.02 |
| Example 2 | −41.06 | −40.82 | −40.35 | −40.74 |
| Comparison Example 1 | 38.01 | 42.87 | 45.90 | 46.89 |
| Comparison Example 2 | 1.37 | 3.96 | 5.77 | 6.65 |

These results show the reference electrode of the present embodiment develops a potential having little dependence upon temperature, and that temperature dependence decreases with an increase in the concentration of the sodium chloride in the agar-agar. In particular, it is safe to say that potential is entirely independent of temperature when the sodium chloride concentration reaches saturation. Accordingly, the reference electrode will operate stably even in a system attended by changes in temperature.

EXAMPLES 3 AND 4, AND COMPARISON EXAMPLES 3 AND 4

Reference electrodes were fabricated through a procedure similar to that used in Example 2 except for the fact that the proportions of the silver chloride and silver oxide constituting the sintered body of the electrode section were varied as shown in Table 3.

TABLE 3

| Reference Electrode | AgCl (wt %) | Ag₂O (wt %) |
|---|---|---|
| Example 3 | 80 | 20 |
| Example 4 | 60 | 40 |
| Comparison Example 3 | 40 | 60 |
| Comparison Example 4 | 20 | 80 |

EXPERIMENT NO. 2

Figure 4:
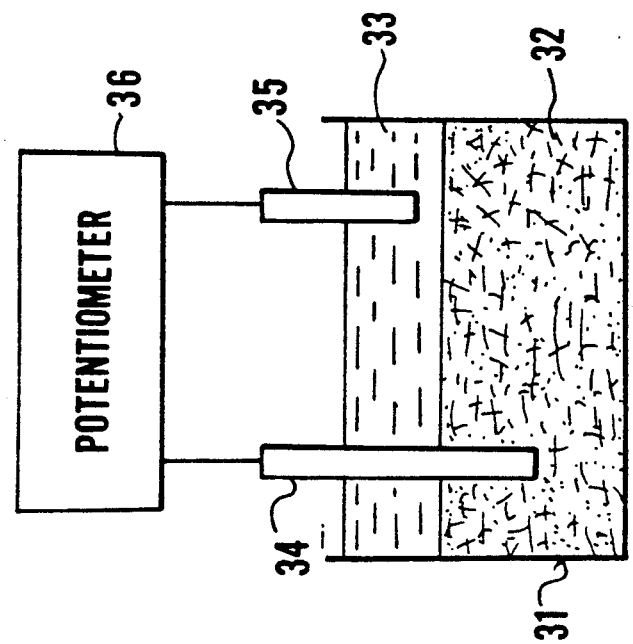
FIG. 4 is a schematic view of a measuring apparatus for measuring the characteristics of the reference electrode according to Examples 3 and 4 of the present invention.

As shown in FIG. 4, a cell 31 was filled with agar-agar gel 32 containing saturated concentrations of sodium chloride and silver chloride, a reference electrode 34 in accordance with each of the Examples 3, 4 and Reference Examples 3, 4 was immersed in the gel 32, an aqueous saturated sodium chloride solution 33 was introduced onto the gel 32, a readily available SSCE 35 was immersed in the sodium chloride solution 33, and the potential difference across the electrodes 34, 35 was measured by a potentiometer 36. The aqueous saturated sodium chloride solution 33 was then removed, the cell 31 containing the agar-agar gel 32 inclusive of the electrode 34 was submitted to autoclave sterilization at 121° C. for 20 min, and the potential difference was measured by the potentiometer 36 as before. The results are as shown in Table 4.

TABLE 4

| | Potential Difference (mV) | |
|---|---|---|
| Reference Electrode | Before Sterilization | After Sterilization |
| Example 3 | −41.51 | −42.03 |
| Example 4 | −41.58 | −41.81 |

TABLE 4-continued

| Reference Electrode | Potential Difference (mV) | |
|---|---|---|
| | Before Sterilization | After Sterilization |
| Comparison Example 3 | −41.62 | −483.13 |
| Comparison Example 4 | −41.87 | −496.1 |

These results show that the reference electrodes of Examples 3 and 4 are almost entirely unaffected by autoclave sterilization, and that reference electrodes having a sintered body containing no less than 60 wt % silver chloride exhibit stable potentials before and after sterilization.

EXAMPLES 5 AND 6, AND COMPARISON EXAMPLES 5 AND 6

Reference electrodes were fabricated through a procedure similar to that used in Example 2 except for the fact that a silver wire having a diameter of 0.2 mm was used as the conductor and the mixture ratios of the silver chloride and silver oxide were varied as shown in Table 5.

TABLE 5

| Reference Electrode | AgCl (wt %) | Ag$_2$O (wt %) |
|---|---|---|
| Example 5 | 80 | 20 |
| Example 6 | 60 | 40 |
| Comparison Example 5 | 40 | 60 |
| Comparison Example 6 | 20 | 80 |

EXPERIMENT NO. 3

In a measurement system similar to that used in Example 1, the pH dependence of the potentials developed by the reference electrodes of Examples 5, 6 and 3, 4 and of Comparison Examples 3, 4 and 5, 6 were measured while varying the pH of the buffer solution. The results are as shown in Table 6.

TABLE 6

| Reference Electrode | Potential Diff. (mV) | Reference Electrode | Potential Diff. (mV) |
|---|---|---|---|
| Ex. 5 | 0.077 × pH −42.98 | Ex. 3 | 0.459 × pH −41.45 |
| Ex. 6 | 0.015 × pH −41.63 | Ex. 4 | 0.220 × pH −40.79 |
| Comp. Ex. 5 | 0.097 × pH −41.47 | Comp. Ex. 3 | 0.219 × pH −41.40 |
| Comp. Ex. 6 | 0.034 × pH −41.26 | Comp. Ex. 4 | 0.135 × pH −40.84 |

These results show that using the silver wire instead of the platinum wire as the conductor provides a greater reduction in pH dependence, and that reference electrodes having a sintered body containing no less than 60 wt % silver chloride are almost entirely independent of pH.

Though not indicated in the above-described Examples, it will be apparent from the Examples that follow that the liquid-junction portion is not limited to a porous ceramic obtained by compacting a mixture of zirconium silicate powder and carbon powder and sintering the mixture in an electric furnace. The liquid-junction portion can be a plug provided with an ion permeable portion having a predetermined diffusion coefficient and volume.

EXAMPLES 7 THROUGH 9

Figure 5:
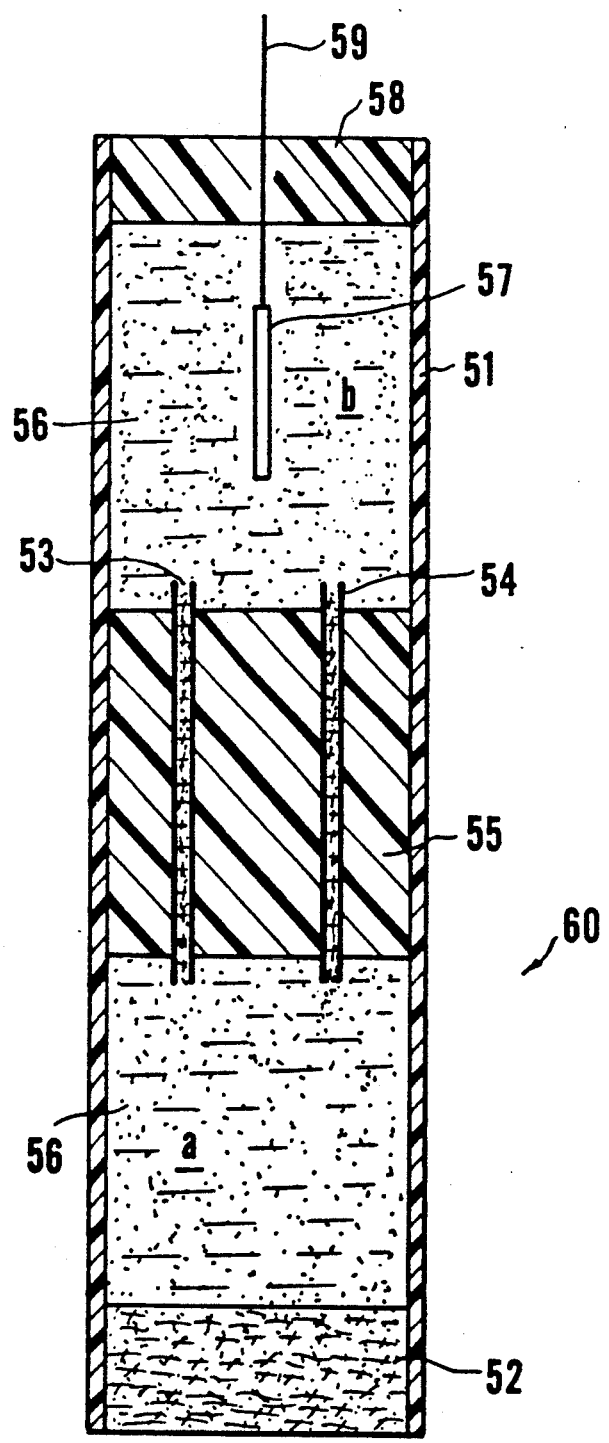
FIG. 5 is a sectional view illustrating a reference electrode according to Examples 7 through 9 of the present invention.

FIG. 5 illustrates the structure of a reference electrode 60 according to an Example 7. The reference electrode 60 includes a hollow insulative tubular body 51 in one open end of which is fixedly secured a plug 52 serving as a liquid-junction portion. The tubular body 51 preferably is made of Teflon, and the plug 52 comprises a porous ceramic filter. The latter can be fabricated by compacting powders of zirconium silicate and carbon at a mixture ratio of 100:30, followed by sintering the mixture at 1,200° C. for 1 hr.

Accommodated within the hollow tubular body 51 is an ion permeable portion comprising a cation exchange layer 53 and an anion exchange layer 54 which are fixedly secured within the tubular body by a urethane resin forming a partitioning wall 55 that divides into two portions a water-containing gel 56 filling the tubular body. The cation layer 53 has a length of 15 mm, a width of 1 mm and a thickness of 0.2 mm, the main chain whereof is a fluorocarbon. An example is Nafion 117 (manufactured by Dupont), having a diffusion coefficient of $7 \times 10^{-8}$ cm$^2$/sec. The anion exchange layer 54 has a length of 15 mm, a width of 1 mm and a thickness of 0.3 mm, the main chain whereof is a fluorocarbon. An example is MA-43 (manufactured by Toyo Soda K.K.), having a diffusion coefficient of $6 \times 10^{-8}$ cm$^2$/sec. About 2 mm of the ion-exchange layers 53, 54 are left exposed to the gel 56 at each end thereof.

The ion-exchange layers 53, 54 and the partitioning wall 55 comprising the urethane resin partition the interior of the tubular body 51 into cells a and b filled with the gel 56. The latter is agar-agar gel containing saturated sodium chloride as an electrolyte. A silver/silver chloride electrode 57 having a conductor wire 59 is inserted into the cell b and secured therein by a urethane resin. A plug 58 is formed at this end of the tubular body, namely at the end opposite the plug 52 serving as the liquid-junction portion. The conductor wire 59 is passed through the plug 58 to lead the electrode 57 to the exterior of the tubular body. This completes the fabrication of the electrode 60 having the structure shown in FIG. 5.

The ion diffusion coefficient (D) of the electrolyte in the ion permeable section comprising the ion-exchange layers 53, 54 preferably is $10^{-7}$–$10^{-10}$ cm$^2$/sec, especially $10^{-8}$–$10^{-9}$ cm$^2$/sec, at 25° C. The volume preferred for the ion permeable section is 0.01–6 mm$^3$. The plug 52 serving as the liquid-junction portion is permeable to ion molecules having a size on the order of 1–50 Å. This means that the plug 52 will not pass molecules whose size exceeds the above mentioned range.

As shown in Table 7, reference electrodes having both the cation- and anion-exchange layers, the cation-exchange layer alone and the anion-exchange layer alone.

TABLE 7

| Example | Ion-Exchange Layer Used |
|---|---|
| 7 | Cation- and anion-exchange layers in parallel |
| 8 | Anion-exchange layer only |
| 9 | Cation-exchange layer only |

Where the ion migration mechanism will now be described using the reference electrode of Example 7, which is shown in FIG. 5.

The following equilibrium reaction takes place in cell b at the silver/silver chloride electrode:

$$AgCl + e^- \rightarrow Ag + Cl^-$$

As a result of this reaction, the following electrode potential E is generated:

$$E = E° + RT/F \cdot \ln(a_c-)$$

where E° represents the potential of the silver/silver chloride electrode, $a_c-$ is the activity of chlorine ion, $ac^- = \gamma \times [Cl^-]$ (note that $[Cl^-]$ represents the $Cl^-$ ion concentration and $\gamma$ represents the activity coefficient), R stands for the gas constant, F the Faraday constant and T the thermodynamic temperature.

Step 1: As a result of a difference in concentration between the liquid specimen and the gel in cell a, $Na^+$ ion and/or $Cl^-$ ion migrate through the specimen.

Step 2: As a result of a difference in concentration between cell a and cell b, $Na^+$ ion and/or $Cl^-$ ion in cell b migrate to cell a.

Accordingly, if the concentration of $Cl^-$ in cell b could be held constant, the electrode would be usable permanently. Owing to the migration of $Cl^-$ ion, however, lifetime is curtailed. This embodiment of the invention is adapted to hold the concentration of $Cl^-$ ion in cell b constant.

EXPERIMENTS 4 THROUGH 6

Figure 6:
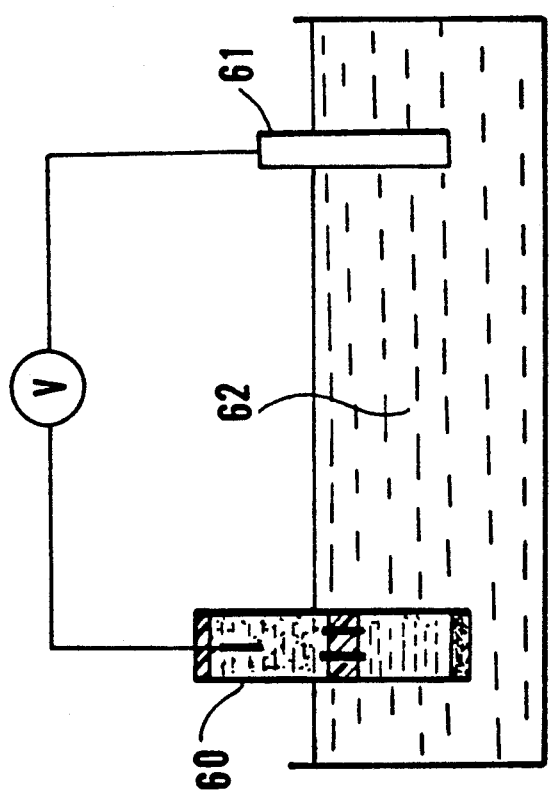
FIG. 6 a circuit diagram illustrating a circuit for measuring the performance of the reference electrode according to Examples 7 through 9 of the present invention.

As shown in FIG. 6, reference electrodes 60 fabricated in accordance with Examples 7 through 9 were immersed in a 50 mM phosphate buffer solution having a pH of 7.4. The electrodes were withdrawn from the solution after 0, 25, 45, 161 and 288 hr and then immersed together with a readily available SSCE 61 in a phosphate buffer solution 62 (pH 7.4, 50 mM) containing 0.154 M sodium chloride. Potential with respect to the SSCE 61 was measured. The results are as shown in Table 8.

Almost no difference among the reference electrodes of Examples 7, 8, 9 was noticed after 45 hr of immersion. After 161 hr of immersion, however, the potential of Example 8 shifted in the positive direction and that of Example 9 shifted in the negative direction. In Example 7, on the other hand, the effects of the cation-exchange layer and anion exchange layer offset each other an no potential shift of the magnitudes was observed. Thus, a highly stable potential was obtained.

potential after 288 hours, indicating that the electrode cannot withstand long use.

The above results show that use of the cation- and anion-exchange layers of the kind employed in Example 7 provided a reference electrode in which the outflow of chloride ion is prevented, whereby there is obtained a stable potential over an extended period of time.

EXAMPLE 10

Figure 7:
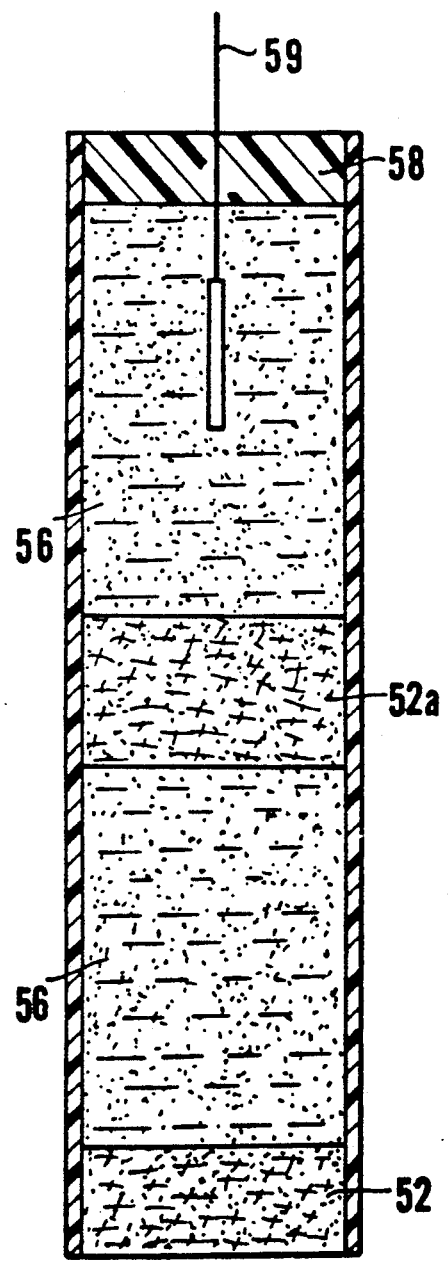
FIG. 7 is a sectional view illustrating a reference electrode according to an example used for comparison purposes.
Figure 8:
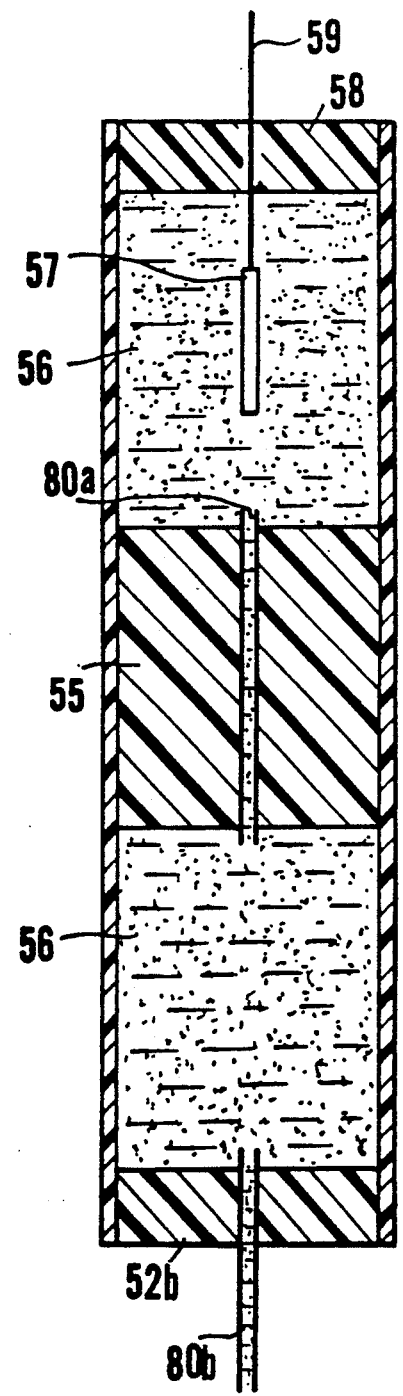
FIGS. 8 and 9 are sectional views of reference electrodes according respectively to Examples 10 and 11 of the present invention.

As shown in FIG. 8, a reference electrode was fabricated using a plug 52b having a capillary tube 80b in place of the plug 52 serving as the liquid-junction portion. In addition, the ion permeable section employed a capillary tube 80a in place of the ion-exchange layer 53, 54. Other portions identical with those shown in FIG. 7 are designated by like reference characters.

A hollow fiber of regenerated cellulose having a length of 25 mm, an inner diameter of 203 μm, an outer diameter of 255 μm and a diffusion coefficient of 5 × 10 cm¹/sec was used as the capillary tubes 80a, b. The lower capillary tube 80 was fixed in the lower hollow insulative tubular body 51 by a urethane bonding agent. The other capillary tube 80 was passed through and secured within the partitioning wall 55 and the plug 52b. Introduced under pressure from the other end of the hollow insulative tubular body 51 was agar-agar gel (agar-agar concentration: 2 wt %) containing saturated sodium chloride, whereby the interior of the tubular body 51 and the interiors of the regenerated cellulose hollow fibers were filled with the agar-agar gel. Another method which can be used is to dip the end portion not having the regenerated cellulose hollow fiber secured thereto into the aforementioned agar-agar gel and then lower the pressure inside the cellulose hollow fibers and tubular body 51 to fill them with the gel. Next, the silver/silver chloride electrode 57 was inserted into the tubular body 51 to complete the fabrication of the reference electrode.

EXPERIMENT 7

The abovementioned reference electrode was dipped in a 50 mM phosphate buffer solution of pH 7.4 and was withdrawn after 20, 45, 161 and 288 hr. Then, as shown in FIG. 6, the electrode was immersed together with the readily available SSCE 61 in the 50 mM phosphate buffer solution 62 (pH 7.4) containing 0.154 M sodium

TABLE 8

| | | \multicolumn{7}{c}{Immersion Time (hour)} | | | | | | |
|---|---|---|---|---|---|---|---|---|
| | | 0 | 1 | 3 | 20 | 45 | 161 | 288 |
| Example 7 | Potential (mV) (vs. SSCE) | −49.3 | — | — | −47.9 | −46.8 | −49.6 | −50.3 |
| Example 8 | Potential (mV) (vs. SSCE) | −49.2 | — | — | −47.8 | −46.9 | −40.5 | −38.5 |
| Example 9 | Potential (mV) (vs. SSCE) | −48.7 | — | — | −47.2 | −51.1 | −55.1 | −60.1 |
| | Potential (mV) (vs. SSCE) | −48.3 | — | — | −47.02 | −46.69 | −47.34 | −46.74 |
| Example 10 | Chlorine Ion Concentration (ppm) | 0 | — | — | 1.02 | 1.82 | 2.3 | 3.3 |
| Comparison | Potential (mV) (vs. SSCE) | −48.25 | — | — | −47.72 | −49.13 | −35.12 | −28.92 |
| | Chlorine Ion Concentration (ppm) | 0 | 0 | 0.45 | 4.3 | 7.75 | 10.6 | 13.0 |

As a comparison example, a reference electrode having a double-junction structure shown in FIG. 7 was fabricated using a porous ceramic filter as the plug 52 and the partitioning wall 52a serving as the liquid-junction portion. The potential of this reference electrode with respect to the SSCE 61 was measured after 0, 20, 45, 101 and 288 hr through the same method as that employed in Examples 7 through 9. The results are as shown in Table 8. It was found that the reference electrode having this structure develops a sudden rise in chloride. Potential with respect to the SSCE 31 was measured. The concentration of chlorine ion which flowed out into the 50 mM phosphate buffer solution from the reference electrode was measured by colorimetry. The results are shown in Table 8 in the same manner as the results of Experiments 4 through 6.

It is evident from the results that the reference electrode using the regenerated cellulose hollow fibers exhibited little chlorine ion outflow and a stable potential over an extended period of time.

EXAMPLE 11

Figure 9:
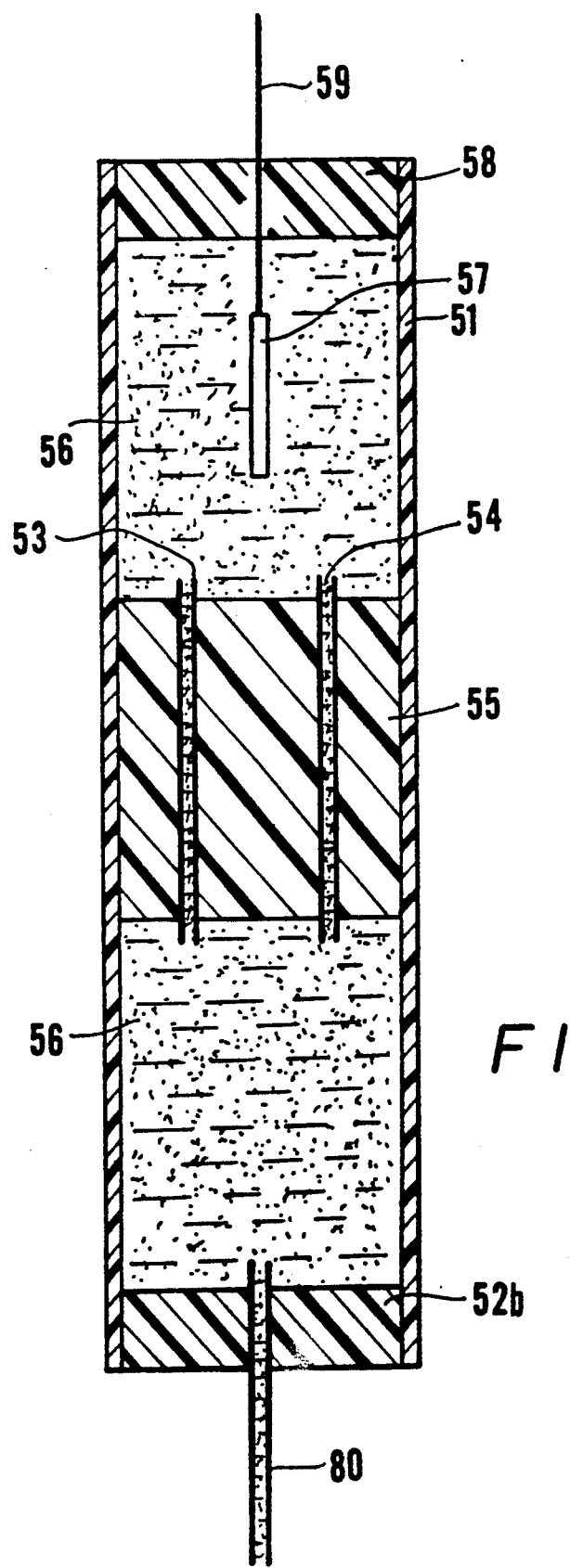

As shown in FIG. 9, a reference electrode was fabricated having the ion-exchange layers provided between the cells a and b and the plug 52b provided with the capillary tube 80 comprising a regenerated cellulose hollow fiber. This reference electrode exhibited a stable potential over an extended period of time, just as the reference electrode of Example 10.

It should be noted that the cation- and anion-exchange layers and the regenerated cellulose hollow fibers can be plural in number. Also, the electrolyte is not limited to chlorine compounds such as sodium chloride and potassium chloride mentioned in the foregoing examples, and other halide compounds can be used if desired. The technical concept of the invention resides in a reference electrode which, while fulfilling its function as a reference electrode, exhibits less outflow of ions to a liquid specimen. To this end, the amount of ion permeation (diffusion coefficient, etc.) is set within a predetermined range. The method of achieving this is not limited to that of the foregoing examples.

As many apparently widely different embodiments of the present invention can be made without departing from the spirit and scope thereof, it is to be understood that the invention is not limited to the specific embodiments thereof except as defined in the appended claims.

What is claimed is:

1. A reference electrode comprising:
   an electrical conductor consisting of platinum or silver;
   a sintered body on the electrical conductor formed of a mixture of silver halide and silver oxide;
   a water-containing gel enveloping said sintered body and containing a halogen ion electrolyte;
   a hollow tubular body accommodating said water-containing gel and having one end closed by a first liquid-junction portion and its other end liquid-tightly sealed by a plug; and
   a conductor wire connected to the electrical conductor and extended to pass through the plug liquid tightly.

2. The reference electrode according to claim 1, wherein said first liquid-junction portion comprises a porous ceramic including a silicate and carbon.

3. The reference electrode according to claim 1, wherein said water-containing gel is selected from the group consisting of polyvinyl alcohol, polyacrylic amide, agar-agar, gelatin, mannon and starch.

4. The reference electrode according to claim 1, wherein said halogen ion is supplied to said water-containing gel by sodium chloride.

5. The reference electrode according to claim 1, wherein said first liquid-junction portion comprises an ion impermeable wall penetrated by an ion permeable portion permeable to said halogen ion and having a pre-determined diffusion coefficient and volume.

6. The reference electrode according to claim 5, wherein said water-containing gel is selected from the group consisting of polyvinyl alcohol, polyacrylic amide, agar-agar, gelatin, mannon and starch.

7. The reference electrode according to claim 5, wherein said halogen ion is supplied to said water-containing gel by sodium chloride.

8. The reference electrode according to claim 5, wherein the diffusion coefficient of said ion permeable portion ranges from $10^{-7}$ to $10^{-10}$ cm$^2$/sec and the volume thereof ranges from 0.01 to 6 mm$^3$.

9. The reference electrode according to claim 5, wherein said ion permeable portion comprises an ion exchange resin layer.

10. The reference electrode according to claim 5, wherein said ion permeable portion comprises an anion exchange resin layer and a cation-exchange resin layer.

11. The reference electrode according to claim 5, wherein said ion permeable portion comprises a hollow fiber filled with the water-containing gel containing the halogen ion electrolyte.

12. The reference electrode according to claim 11, wherein said hollow fiber comprises an ion permeable hydrophilic polymer or an ion permeable hydrophobic polymer.

13. The reference electrode according to claim 5, wherein said water-containing gel is a natural high polymer.

14. The reference electrode according to claim 1, further comprising a second liquid-junction portion partitioning said water-containing gel into at least two portions.

15. The reference electrode according to claim 14, wherein at least one of said first and second liquid-junction portions comprises an ion impermeable wall penetrated by an ion permeable portion permeable to said halogen ion and having a predetermined diffusion coefficient and volume, and the diffusion coefficient of said ion permeable portion ranges from $10^{-7}$ to $10^{-10}$ cm$^2$/sec and the volume thereof ranges from 0.01 to 6 mm$^3$.

16. The reference electrode according to claim 15, wherein said ion permeable portion comprises an ion exchange resin layer.

17. The reference electrode according to claim 15, wherein said ion permeable portion comprises an anion exchange resin layer and a cation-exchange resin layer.

18. The reference electrode according to claim 15, wherein said ion permeable portion comprises a hollow fiber filled with the water-containing gel containing the halogen ion electrolyte.

19. The reference electrode according to claim 18, wherein said hollow fiber comprises an ion permeable hydrophilic polymer or an ion permeable hydrophobic polymer.

20. The reference electrode according to claim 14, wherein at least one of said first and second liquid-junction portions comprises a porous ceramic including a silicate and carbon.

21. The reference electrode according to claim 1, wherein said water-containing gel is a natural high polymer.

* * * * *

UNITED STATES PATENT AND TRADEMARK OFFICE
CERTIFICATE OF CORRECTION

PATENT NO. : 5,071,537
DATED : December 10, 1991
INVENTOR(S) : Shuichiro YAMAGUCHI, et al.

It is certified that error appears in the above-identified patent and that said Letters Patent is hereby corrected as shown below:

In column 9, line 44, "an" is changed to --and--

In column 10, lines 19-20, "$5 \times 10 \text{ cm}^1/\text{sec}$" is changed to --$5 \times 10^{-7} \text{ cm}^2/\text{sec}$--

Signed and Sealed this

Fourth Day of May, 1993

Attest:

MICHAEL K. KIRK

*Attesting Officer*   Acting Commissioner of Patents and Trademarks